United States Patent
Markusson et al.

(10) Patent No.: US 11,679,071 B2
(45) Date of Patent: Jun. 20, 2023

(54) UROGENITAL CLEANSING COMPOSITION

(71) Applicant: PEPTONIC MEDICAL AB, Bromma (SE)

(72) Inventors: Dan Markusson, Växjö (SE); Anders Carlsson, Stockholm (SE); Erik Sundquist, Saltsjöbaden (SE)

(73) Assignee: PEPTONIC MEDICAL AB, Bromma (SE)

( * ) Notice: Subject to any disclaimer, the term of this patent is extended or adjusted under 35 U.S.C. 154(b) by 0 days.

(21) Appl. No.: 17/998,069

(22) PCT Filed: May 12, 2021

(86) PCT No.: PCT/EP2021/062622
§ 371 (c)(1),
(2) Date: Nov. 7, 2022

(87) PCT Pub. No.: WO2021/228937
PCT Pub. Date: Nov. 18, 2021

(65) Prior Publication Data
US 2023/0138911 A1 May 4, 2023

(30) Foreign Application Priority Data

May 13, 2020 (SE) .................... 2050564-0

(51) Int. Cl.
*A61K 8/73* (2006.01)
*A61K 8/92* (2006.01)
*A61Q 19/00* (2006.01)

(52) U.S. Cl.
CPC .............. *A61K 8/731* (2013.01); *A61K 8/922* (2013.01); *A61Q 19/005* (2013.01); *A61K 2800/33* (2013.01)

(58) Field of Classification Search
None
See application file for complete search history.

(56) References Cited

FOREIGN PATENT DOCUMENTS

WO    WO 2018/219747 A1    12/2018

OTHER PUBLICATIONS

Database GNPD Mintel: Aug. 13, 2019, anonymous: "Soothing Protective Shower Gel", XP055835980, Database accession No. 6790551.
Database GNPD Mintel: Nov. 6, 2018, anonymous: "Body and Intimate Shower Cream", XP055835982, Databse accession No. 6105265.
International Search Report and Written Opinion were dated Sep. 21, 2021 by the International Searching Authority for International Application No. PCT/EP2021/062622 filed on May 12, 2021 and published as WO 2021228937 (Applicant—Peptonic Medical AB) (10 pages).

*Primary Examiner* — Nicole P Babson
(74) *Attorney, Agent, or Firm* — Ballard Spahr LLP

(57) ABSTRACT

Described is a urogenital cleansing composition that includes a non-ionic cellulose ether, an aqueous solvent, a triglyceride oil and a pH-regulating agent, wherein the urogenital cleansing composition does not contain any additional emulsifier and have a pH within the range of from 3 to 4 and wherein the pH-regulating agent is a lactate buffer.

20 Claims, No Drawings

UROGENITAL CLEANSING COMPOSITION

CROSS-REFERENCE TO RELATED APPLICATIONS

This application is a U.S. National Phase Application of International Application No. PCT/EP2021/062622, filed May 12, 2021, which claims priority to Swedish Application No. 2050564-0, filed May 13, 2020, each of which are hereby incorporated by reference in their entirety.

TECHNICAL FIELD

The present document discloses a urogenital cleansing composition comprising a non-ionic cellulose ether and a triglyceride oil, wherein the urogenital cleansing composition does not contain any additional emulsifier.

BACKGROUND

The intimate skin of the urogenital area, such as the lower abdomen, is highly fragile and sensitive with its mucous membrane being irritated easily.

Consequently, it may be difficult to clean the urogenital area without affecting the mucous membrane in an adverse way. Accordingly, cleansing compositions intended for the urogenital area have particular requirements in order to function in the delicate, sensitive, and fragile intimate skin area of the lower abdomen.

An object of the present document is to alleviate at least one of the problems discussed above, and to provide advantages and aspects not provided by hitherto known technique.

SUMMARY

The present document provides a urogenital cleansing composition comprising:
i) at least one non-ionic cellulose ether;
ii) an aqueous solvent, such as water;
iii) at least one triglyceride oil;
iv) a pH-regulating agent,
the composition having a pH within the range of from 3 to 4, wherein the non-ionic cellulose ether, the aqueous solvent, the triglyceride oil, and the pH-regulating agent are homogenously mixed, wherein the composition does not contain any additional emulsifier, and wherein the pH-regulating agent is a lactate buffer.

The present document further provides a method for preparing a urogenital cleansing composition as disclosed herein, the method comprising the steps of:
i) providing an aqueous gel comprising at least one non-ionic cellulose ether and a pH-regulating agent;
ii) providing at least one triglyceride oil;
iii) mixing the aqueous gel comprising the non-ionic cellulose ether and the pH-regulating agent with the triglyceride oil so that a homogenous mixture is obtained, wherein the aqueous gel comprising the non-ionic cellulose ether and the pH-regulating agent has a viscosity of from 35 000 to 100 000 mPas, and wherein the aqueous gel comprising the non-ionic cellulose ether and the pH-regulating agent has an osmolality from 10 to 300 mOsmol/kg, optionally from 10 to 200 mOsmol/kg, optionally from 20 to 100 mOsmol/kg, optionally from 30 to 50 mOsmol/kg.

The present document is also directed to a urogenital cleansing composition as disclosed herein prepared by a method as disclosed herein.

Other features and advantages of the present document will be apparent from the following detailed description, drawings, examples, and from the claims.

DETAILED DESCRIPTION

The present inventors have surprisingly found that it is possible to produce a homogenous and stable composition comprising a non-ionic cellulose ether and a triglyceride oil without the use of an additional emulsifier and being particularly suited for cleansing of the urogenital area. The urogenital area is a highly sensitive area and cleansing compositions intended for this area have particular requirements compared to cleansing compositions intended for other parts of the body, such as facial cleansing composition.

The present document thus provides a urogenital cleansing composition comprising:
i) at least one non-ionic cellulose ether;
ii) an aqueous solvent, such as water;
iii) at least one triglyceride oil;
iv) a pH-regulating agent,
the composition having a pH within the range of from 3 to 4, wherein the non-ionic cellulose ether, the aqueous solvent, the triglyceride oil, and the pH-regulating agent are homogenously mixed, wherein the composition does not contain any additional emulsifier, and wherein the pH-regulating agent is a lactate buffer.

The present urogenital cleansing composition is thus for cleansing of the urogenital area, such as the delicate intimate skin areas in the lower abdomen. The fact that the composition comprises a non-ionic cellulose ether, a triglyceride oil and a pH regulating agent without the use of an additional emulsifier in combination with that the urogenital cleansing composition has a pH within the range of from 3 to 4 with the pH regulating agent being a lactate buffer has been found to provide a surprisingly effective cleansing feeling leaving the consumers a feeling of being rehydrated and not dehydrated after use. Hence, the urogenital cleansing composition as disclosed herein is a cleanser which gently wash without de-hydrating and without disturbing the pH balance of the delicate intimate skin in the urogenital area. If pH rises in the urogenital area, it can damage cells, cause infection and the skin can become red and dry. Consequently, the urogenital cleansing composition as disclosed herein do not irritate the mucous membrane in the urogenital area.

The urogenital cleansing composition may be denoted an oil-in-water composition.

The non-ionic cellulose ether, aqueous solvent and triglyceride oil are homogenously mixed, and stay homogenously mixed upon storage, despite the lack of an additional emulsifier. By homogenously mixed is in the context of the present document intended that the components are mixed so that one, uniform system is formed.

The at least one non-ionic cellulose ether may be dissolved in the aqueous solvent, thus forming an aqueous non-ionic cellulose ether gel, before being mixed with the triglyceride oil.

When preparing the urogenital cleansing composition of the present document, an aqueous gel comprising a non-ionic cellulose ether and any other ingredients may first be prepared prior to being mixed with the triglyceride oil.

Hence, the at least one non-ionic cellulose ether and the pH-regulating agent, such as the lactate buffer, may be dissolved in the aqueous solvent, thus forming an aqueous non-ionic cellulose ether gel comprising a non-ionic cellulose ether and pH-regulating agent, such as a lactate buffer, before being mixed with the triglyceride oil.

The aqueous non-ionic cellulose ether gel, comprising a non-ionic cellulose ether and a pH-regulating agent may, prior to including the triglyceride oil, have a viscosity of from 35 000 to 100 000 mPas, optionally from 38 000 to 100 000 mPas, optionally from 40 000 to 100 000 mPas, optionally from 45 000 to 100 000 mPas, optionally from 47 000 to 100 000 mPas, optionally from 50 000 to 100 000 mPas, optionally from 52 000 to 100 000 mPas or optionally from 55 000 to 100 000 mPas. By mixing a non-ionic cellulose ether gel having such viscosity with a triglyceride oil in order to achieve a urogenital cleansing composition, it has been found by the present inventors that an improved urogenital cleansing composition may be provided with a stable and pleasant consistency and that is easily applicable. Since the consistency is viscous and not too liquid, the urogenital cleansing composition according to the present document remains in the area during washing, but may at the same time easily be rinsed off, so that no undesired residues of the urogenital cleansing composition remains after cleansing/washing which may otherwise lead to irritation and dehydration of the mucous membrane. Such viscosity of the aqueous non-ionic cellulose ether gel furthermore favours further mixing with the triglyceride oil in order to achieve the urogenital cleansing composition as disclosed herein.

The non-ionic cellulose ether gel may have an osmolality within the range of from 10 to 300 mOsmol/kg, optionally from 10 to 200 mOsmol/kg, such as from 20 to 100 mOsmol/kg, or optionally from 30 to 50 mOsmol/kg. By mixing a non-ionic cellulose ether having such osmolality with a triglyceride oil an improved urogenital cleansing composition preventing the mucosal membrane of the urogenital area to de-hydrate upon use of the urogenital cleansing composition may be provided.

Further, the urogenital cleansing composition as disclosed herein may have a viscosity of from 40 000 to 55 000 mPas. This has been found to provide an enhanced effect of generating a stable and pleasant consistency of the urogenital cleansing composition that is easily applicable and not too liquid. The urogenital cleansing composition thus remains in the area during washing but is at the same time easily rinsed off, so that no undesired residues of the urogenital cleansing composition remains after cleansing/ washing. This is of particular importance for the urogenital area, both since it is a sensitive area, but also since complete rinsing may be more difficult in this area comprising skin creases and folds.

The triglyceride oil (or triacylglycerol) may preferably be a vegetable oil. The triglyceride oil may be a long chain triglyceride oil, such as oat oil, olive oil, sunflower oil, or rapeseed oil. The triglyceride oil is typically a medium-chain or long-chain triglyceride oil. Non-limiting examples of long-chain triglyceride oils are soybean oil, olive oil, sunflower oil, rapeseed (e.g. canola) oil and oat oil. Medium-chain triglyceride oils are prepared industrially by esterification of glycerol with octanoic and decanoic acids, obtained from coconut and palm kernel oils. The triglyceride oil may be liquid at room temperature and then denoted a triglyceride oil. This has been found to provide an enhanced effect of generating a urogenital cleansing composition provided with both a cleansing and emollient effect. Traces of the triglyceride oil, which is good for the skin in the urogenital area, remain in the urogenital area after cleansing, thus leaving a pleasant soft feeling after use.

The urogenital cleansing composition may comprise just one triglyceride oil or a mixture of two or more triglyceride oils, such as 2, 3, 4, 5 or 6 different kinds of triglyceride oils.

When two or more different triglyceride oils are present in the composition, the ratio between the different triglyceride oils may be the same or different. This has been found to provide a urogenital cleansing composition with a cleansing and emollient effect, leaving a soft feeling after use.

The non-ionic cellulose ether may be selected from the group consisting of methylcellulose (MC), hydroxypropylcellulose (HPC), hydroxypropylmethylcellulose (HPMC), hydroxyethylethylcellulose (HEEC) and hydroxyethylmethylcellulose (H EMC) and any combination thereof. The composition may comprise only one kind of non-ionic cellulose ether or a mixture of two or more different kinds of non-ionic cellulose ethers, such as 2, 3, 4 or 5 different kinds of non-ionic cellulose ethers. At least one of the non-ionic cellulose ether may e.g. be hydroxypropylmethylcellulose (HPMC). This has been found to provide a thickening and stabilizing effect on the non-ionic cellulose ether gel thus facilitating further mixing with a triglyceride oil.

The triglyceride oil may constitute from 1 to 20 wt %, such as 1-18 wt %, optionally 1-15 wt %, 5-20 wt %, or optionally 5-15 wt % based on the total weight of the urogenital cleansing composition. This has been found to provide a urogenital cleansing composition having a cleansing and emollient effect, leaving a soft feeling after use.

The amount of non-ionic cellulose ether in an aqueous non-ionic cellulose ether gel used for preparing a composition according to the present document may be from 1 wt % to 5 wt %, such as 1.5 wt %, 2 wt %, 2.5 wt %, 3 wt %, 3.5 wt %, 4 wt %, or 4.5 wt %. This has been found to provide a thickening and stabilizing effect on the non-ionic cellulose ether gel thus facilitating the further mixing with the triglyceride oil.

The urogenital cleansing composition according to the present document may have a pH within the range of from 3.2 to 4.0, optionally from 3.5 to 4.0, or optionally from 3.7 to 3.9, such as 3.8. The pH of the composition as described is regulated by the presence of a pH-regulating agent in the composition, the pH regulating agent being a lactate buffer. The concentration of a pH-regulating agent in a non-ionic cellulose gel used in preparing the composition of the present document may be from 20 to 100 mM, or optionally from 20 to 75 mM, optionally from 20 to 50 mM, optionally from 20 to 40 mM, or optionally from 20 to 30 mM, such as 25 mM, in an aqueous solution. This has been found to provide a urogenital cleansing composition which is particularly adapted for the urogenital area which prevents dehydration of the mucosal membrane upon use.

The urogenital cleansing composition as described herein may further comprise a preservative, such as benzoic acid. This provides an enhanced shelf life of the urogenital cleansing composition.

An aqueous non-ionic cellulose ether gel used for preparing the urogenital cleanings composition of the present document may comprise from 3 wt % to 4 wt %, such as 3 wt % to 3.5 wt %, such as 3.2 wt % hydroxypropylmethylcellulose (HPMC), a lactate buffer in a concentration of from 20 to 40 mM and optionally a preservative, such as benzoic acid, at a concentration of from 0.05 to 0.15 mg/g, the composition having a pH within the range of from 3.5 to 4, such as 3.8. This has been found to provide a urogenital cleansing composition which is particularly adapted for the urogenital area, preventing dehydration of the mucosal membrane upon use.

The urogenital cleansing composition as disclosed herein may consist of at least one non-ionic cellulose ether, a pH-regulating agent, an aqueous solvent, at least one triglyceride oil, and optionally a preservative. This has been found to provide a urogenital cleansing composition which is particularly adapted for the urogenital area, preventing dehydration of the mucosal membrane upon use.

In total, the urogenital cleansing composition may consist of from 1 to 20 wt % triglyceride oil, from 0.8 to 4.0 wt % non-ionic cellulose ether, such as 2.56 wt % hydroxypropylmethylcellulose (HPMC), from 16 to 32 mM of lactate buffer solution, a preservative, such as benzoic acid, from 0.04 to 0.12 wt %, and an aqueous solvent which constitutes the remaining part of the urogenital composition such that the total amount is 100 wt %, the composition having a pH within the range of from 3.5 to 4, such as 3.8. This has been found to provide a urogenital cleansing composition which is particularly adapted for the urogenital area preventing dehydration of the mucosal membrane upon use.

The urogenital cleansing composition as disclosed herein is free from alcohol. The composition of the present document may be administered to the urogenital area one or more times a day, such as 1-5 times a day such as, 1, 2, 3, 4, or 5 times a day.

There is also provided a method for preparing the urogenital cleansing composition described herein, the method comprising the steps of:
i) providing an aqueous gel comprising at least one non-ionic cellulose ether and a pH-regulating agent;
ii) providing at least one triglyceride oil;
iii) mixing the aqueous gel comprising the non-ionic cellulose ether and the pH-regulating agent with the triglyceride oil so that a homogenous mixture is obtained, the pH-regulating agent being a lactate buffer and the aqueous gel comprising the non-ionic cellulose ether and the pH-regulating agent has a viscosity of from 35 000 to 100 000 mPas, and the aqueous gel comprising the non-ionic cellulose ether and the pH-regulating agent has an osmolality from 10 to 300 mOsmol/kg, optionally from 10 to 200 mOsmol/kg, optionally from 20 to 100 mOsmol/kg, optionally from 30 to 50 mOsmol/kg.

When an aqueous non-ionic cellulose ether gel as disclosed herein is mixed with the triglyceride oil, the aqueous gel may, prior to mixing, optionally have a viscosity of from 38 000 to 100 000 mPas, optionally from 40 000 to 100 000 mPas, optionally from 45 000 to 100 000 mPas, optionally from 47 000 to 100 000 mPas, optionally from 50 000 to 100 000 mPas, optionally from 52 000 to 100 000 mPas or optionally from 55 000 to 100 000 mPas.

Further, the present document is also directed to a urogenital cleansing composition as disclosed herein prepared by a method as disclosed herein.

The composition disclosed herein may be denoted a urogenital cleansing composition. The invention will be further described in the following examples, which do not limit the scope of the invention described in the claims Experimental Section

EXAMPLE 1

Method for Preparing Compositions

To a 100 ml glass beaker were added VagiVital (Peptonic Medical AB, containing 3.2 wt % hypromellose Benecel K15M (hydroxypropylmethylcellulose (HPMC)), 25 mM lactate buffer and 0.1% benzoic acid in purified water) and a triglyceride oil in the amounts specified in Tables 1 and 2. The mixture was homogenised for 3 minutes at 10,000 rpm (revolutions per minute) using a rotor/stator homogeniser, such as a DI 25 basic dispersion tool (high-speed dispersion and emulsifying unit from Ika-Werke, Germany). The resulting composition was then stored at room temperature and its stability in terms of homogeneity was observed.

EXAMPLE 2

Comparative Compositions with Emulsifier

Two compositions comprising VagiVital, a medium-chain triglyceride oil and a mild emulsifier were prepared using the method of Example 1 but with the amounts of ingredients according to Table 1. The emulsifier was added after the addition of the triglyceride oil. The batch size was 56 g.

TABLE 1

Compositions with emulsifier, percentages by weight.

| | Concentration VagiVital | Oily components | Appearance |
|---|---|---|---|
| A | 88.8% | 9.2% Crodamol GTCC (INCI: Caprylic/Capric Triglyceride oil) 2.0% Softisan condition hair (INCI: PCA Glyceryl Oleate) | Fine cream at preparation, separation on standing at RT within days |
| B | 88.6% | 9.3% Crodamol GTCC (INCI: Caprylic/Capric Triglyceride oil) 2.1% Softisan PG2 C10 (INCI: Polyglyceryl-2 Caprate) | Fine cream at preparation, separation on standing at RT within weeks |

As can be seen in Table 1, the compositions were homogenous directly after preparation but separated upon storage at room temperature.

EXAMPLE 3

Compositions without Emulsifier

Five compositions comprising VagiVital (according to Example 1) and a triglyceride oil without an emulsifier were prepared using the method of Example 1 but with the amounts of ingredients according to Table 2. The batch size was 56 g.

TABLE 2

Compositions without emulsifier, percentages by weight.

| | Concentration VagiVital | Oily components | Appearance |
|---|---|---|---|
| A | 89.1% | 10.9% Crodamol GTCC (INCI: Caprylic/Capric Triglyceride oil) | Fine cream at preparation, stable for several months |
| B | 90.0% | 10.0% Miglyol 812N (INCI: Caprylic/Capric Triglyceride oil) | Fine cream at preparation, stable for several months |
| C | 90.0% | 10.0% Lipex Preact (INCI: Canola Oil) | Fine cream at preparation, stable for several months |
| D | 90.0% | 10.0% Oat Lipid E (INCI: Avena Sativa (Oat) Kernel Oil) | Fine cream at preparation, stable for several months |
| E | 90.0% | 9.0% Lipex Preact (INCI: Canola Oil) 1.0% Oat Lipid E (INCI: Avena Sativa (Oat) Kernel Oil) | Fine cream at preparation, stable for several months |

As can be seen in Table 2, the compositions comprising hydroxypropylmethylcellulose (HPMC), lactate buffer and benzoic acid in purified water (VagiVital, Peptonic Medical AB) and a triglyceride oil are shown to be stable even though they do not comprise an emulsifier.

EXAMPLE 4

Study—Effects Upon Use of Urogenital Cleansing Composition

Twenty women took part in a study. The women tested a urogenital cleansing composition for cleansing the urogenital area according to the present disclosure daily during 17 days.

The women were thereafter asked to evaluate if they experienced that the urogenital cleansing composition did indeed clean, and if the use of the urogenital cleansing composition gave the impression of feeling hydrated, i.e. not de-hydrated.

The urogenital cleansing composition used in the survey consisted of 75-95 wt % aqueous solvent, 5-10 wt % triglyceride oil, 1-5 wt % non-ionic cellulose ether, 0.2-2 wt % lactate buffer and 0.1-1 wt % benzoic acid and had a pH of 3.7-3.9.

The results are shown in Table 3:

TABLE 3

Questions and answers (Yes or No in % of answers of participants)

| Question | Yes | No |
|---|---|---|
| According to your experience, did the urogenital cleansing composition indeed cleaned? | 95% | 5% |
| Did you feel hydrated? | 95% | 5% |

As can be seen in Table 3, 95% of the women who participated in the survey experienced both that the urogenital cleansing composition indeed cleaned and left a hydrated feeling. It can thus be concluded that the urogenital cleansing composition cleanses without dehydrating the urogenital area.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

Unless expressly described to the contrary, each of the preferred features described herein can be used in combination with any and all of the other herein described preferred features.

The invention claimed is:

1. A urogenital cleansing composition comprising
   i) at least one non-ionic cellulose ether;
   ii) an aqueous solvent;
   iii) at least one triglyceride oil; and
   iv) a pH-regulating agent,
   said urogenital cleansing composition having a pH within the range of from 3 to 4, wherein the at least one non-ionic cellulose ether, said aqueous solvent, the at least one triglyceride oil, and said pH-regulating agent are homogenously mixed, wherein said urogenital cleansing composition does not contain any additional emulsifier, and wherein the pH-regulating agent is a lactate buffer.

2. The urogenital cleansing composition according to claim 1, wherein the at least one non-ionic cellulose ether and said pH-regulating agent are dissolved in said aqueous solvent thus forming a non-ionic cellulose ether gel before mixing with the at least one triglyceride oil.

3. The urogenital cleansing composition according to claim 1, wherein the urogenital cleansing composition has a viscosity of from 40 000 to 55 000 mPas.

4. The urogenital cleansing composition according to claim 1, wherein the at least one triglyceride oil is a vegetable oil.

5. The urogenital cleansing composition according to claim 1, wherein the at least one triglyceride oil is a long-chain triglyceride oil.

6. The urogenital cleansing composition according to claim 1, wherein the at least one triglyceride oil is a medium-chain triglyceride oil.

7. The urogenital cleansing composition according to claim 1, wherein the at least one non-ionic cellulose ether is selected from the group consisting of methylcellulose (MC), hydroxypropylcellulose (HPC), hydroxypropylmethylcellulose (HPMC), hydroxyethylethylcellulose (HEEC), and hydroxyethylmethylcellulose (HEMC), and any combination thereof.

8. The urogenital cleansing composition according to claim 1, wherein at least one of said non-ionic cellulose ether is hydroxypropylmethylcellulose (HPMC).

9. The urogenital cleansing composition according to claim 1, wherein the at least one triglyceride oil constitutes from 1 to 20 wt % of the total weight of the composition.

10. The urogenital cleansing composition according to claim 2, wherein the amount of the at least one non-ionic cellulose ether in said non-ionic cellulose ether gel is from 1 wt % to 5 wt %.

11. The urogenital cleansing composition according to claim 1, wherein said urogenital cleansing composition has a pH within the range of from 3.2 to 4.0.

12. The urogenital cleansing composition according to claim 1, said urogenital cleansing composition further comprises a preservative.

13. The urogenital cleansing composition according to claim 2, wherein said non-ionic cellulose ether gel comprises from 3 wt % to 4 wt % hydroxypropylmethylcellulose (HPMC) and a lactate buffer in a concentration of from 20 to 40 mM, said urogenital cleansing composition having a pH within the range of from 3.5 to 4.

14. The urogenital cleansing composition according to claim 1, said urogenital cleansing composition consisting of the at least one non-ionic cellulose ether, the pH-regulating agent, the aqueous solvent, and the at least one triglyceride oil.

15. The urogenital cleansing composition according to claim 13, wherein the urogenital cleansing composition further comprises a preservative in a concentration from 0.5 to 1.5 mg/g.

16. The urogenital cleansing composition according to claim 2, wherein said non-ionic cellulose ether gel has an osmolality from 10 to 300 mOsmol/kg.

17. The urogenital cleansing composition according to claim 12, wherein the preservative is benzoic acid.

18. The urogenital cleansing composition according to claim 1, wherein the aqueous solvent is water.

19. A method for preparing the urogenital cleansing composition according to claim 1, said method comprising the steps of:
  i) providing an aqueous gel comprising at least one non-ionic cellulose ether and a pH-regulating agent;
  ii) providing at least one triglyceride oil;
  iii) mixing said aqueous gel comprising the at least one non-ionic cellulose ether and said pH-regulating agent, and the at least one triglyceride oil so that a homogenous mixture is obtained,
  wherein the pH-regulating agent is a lactate buffer and wherein said aqueous gel comprising the at least one non-ionic cellulose ether and said pH-regulating agent has a viscosity of from 35,000 to 100,000 mPas, and wherein said aqueous gel comprising the at least one non-ionic cellulose ether and said pH-regulating agent has an osmolality from 10 to 300 mOsmol/kg.

20. The method according to claim 19, wherein said aqueous gel comprising the at least one non-ionic cellulose ether and said pH-regulating agent has a viscosity of from 38,000 to 100,000 mPas.

* * * * *